(12) United States Patent
McAuley et al.

(10) Patent No.: US 6,254,248 B1
(45) Date of Patent: Jul. 3, 2001

(54) CONTROLLED FRAGRANCE DISPENSER FOR LIGHT BULB

(75) Inventors: Gene William McAuley; Diann Looney McAuley, both of Proctor, AR (US)

(73) Assignee: BJM, Inc., Memphis, TN (US)

( * ) Notice: Subject to any disclaimer, the term of this patent is extended or adjusted under 35 U.S.C. 154(b) by 0 days.

(21) Appl. No.: 09/483,747

(22) Filed: Jan. 17, 2000

(51) Int. Cl.$^7$ ........................................... F21V 33/00
(52) U.S. Cl. ........................ 362/101; 362/101; 362/255; 422/4; 422/125
(58) Field of Search ................... 362/96, 101, 255, 362/92; 422/4, 125, 305, 306

(56) References Cited

U.S. PATENT DOCUMENTS

| | | | |
|---|---|---|---|
| 3,930,796 | 1/1976 | Haensel | 21/74 |
| 3,959,642 | * 5/1976 | Turro | 240/2 |
| 4,184,099 | 1/1980 | Lindauer et al. | 313/315 |
| 4,493,011 | * 1/1985 | Spector | 362/96 |
| 4,647,428 | 3/1987 | Gyulay | 422/4 |
| 4,647,433 | 3/1987 | Spector | 422/125 |
| 5,908,231 | 6/1999 | Huff | 362/96 |

* cited by examiner

Primary Examiner—Stephen Husar
Assistant Examiner—John Anthony Ward
(74) Attorney, Agent, or Firm—Walker, McKenzie & Walker, PC

(57) ABSTRACT

A fragrance dispenser for use with a light bulb and fragrance medium that emits a fragrance when heated. The fragrance dispenser includes a body member having an opening for receiving a portion of a light bulb and having a cavity for holding a fragrance medium so that when the fragrance medium is held in the cavity, the light bulb is energized, and at least a portion of the light bulb is received in the opening the body member, heat from the light bulb will be transferred through at least a portion of the body member to the fragrance medium held in the cavity in the body member to cause the fragrance medium to emit a fragrance. The fragrance dispenser additionally includes control structure for controlling the emissions of fragrance from the fragrance medium held in the cavity in the body member.

3 Claims, 5 Drawing Sheets

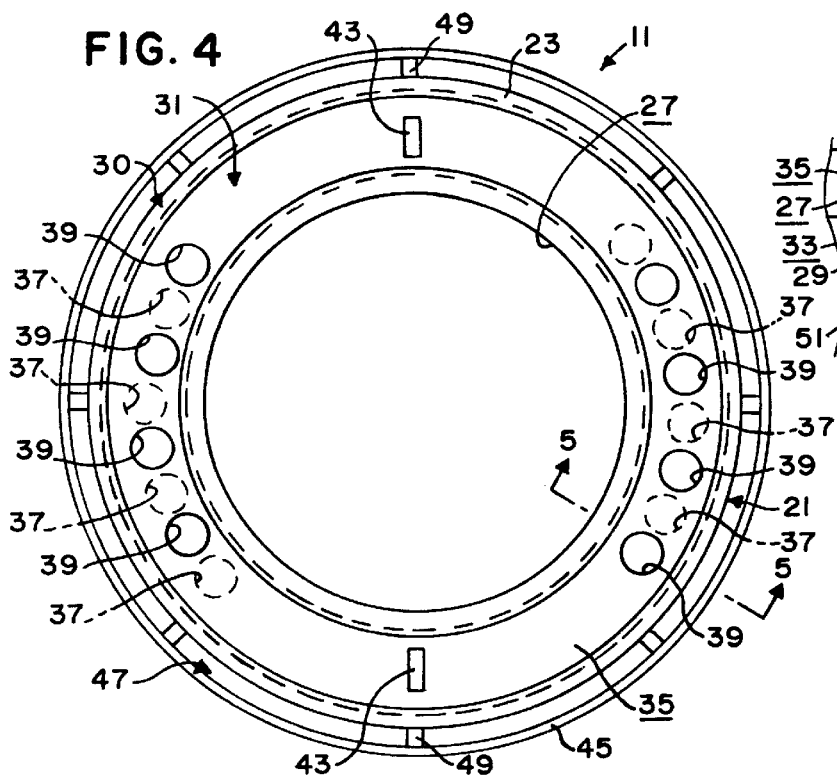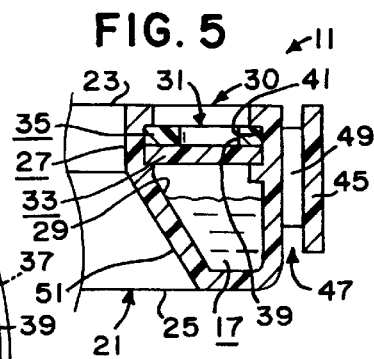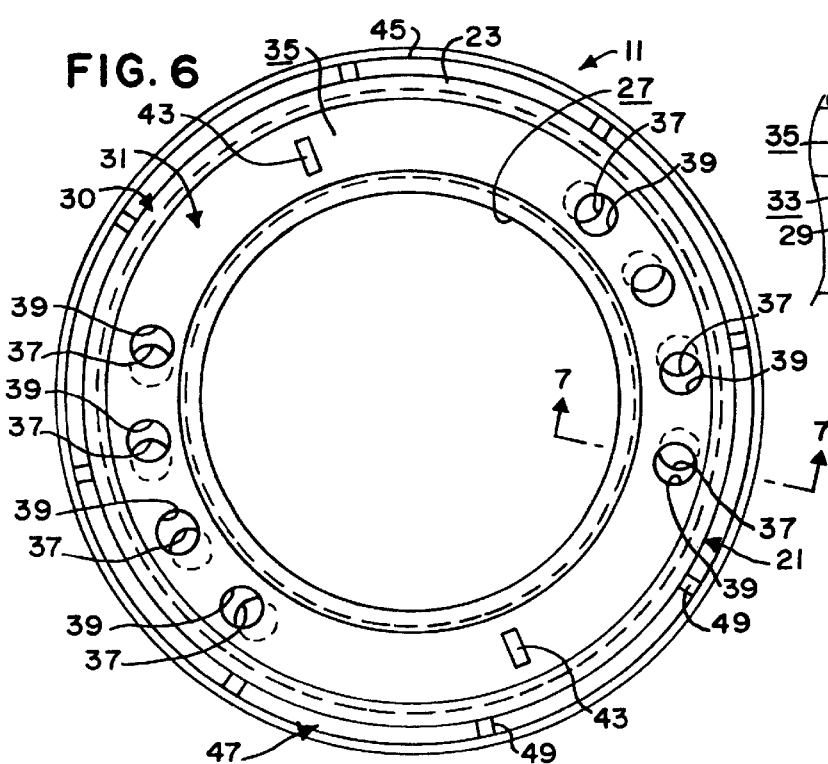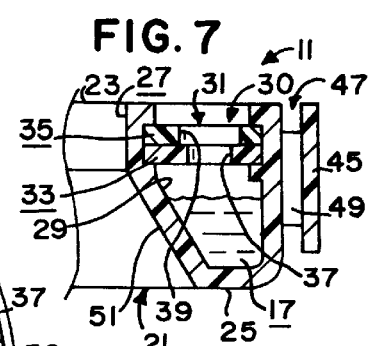

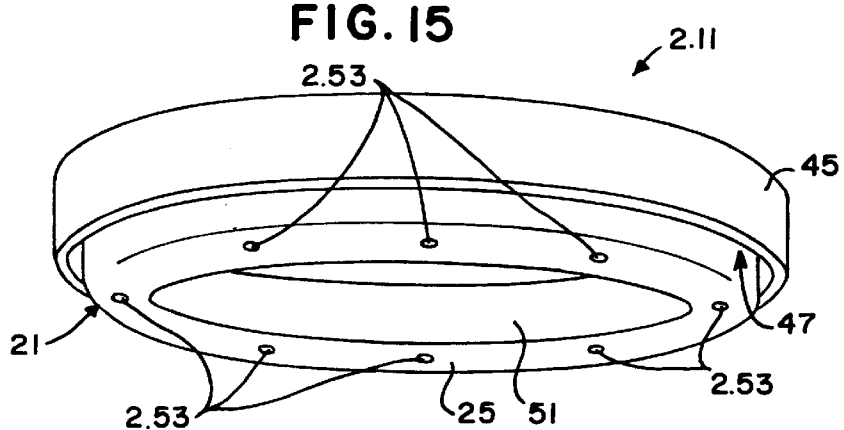
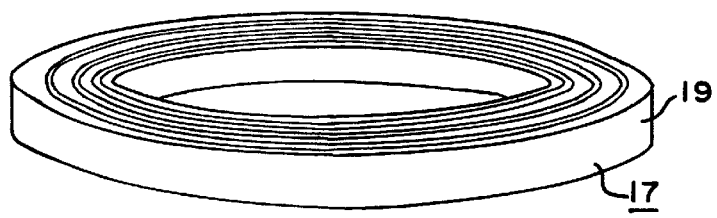
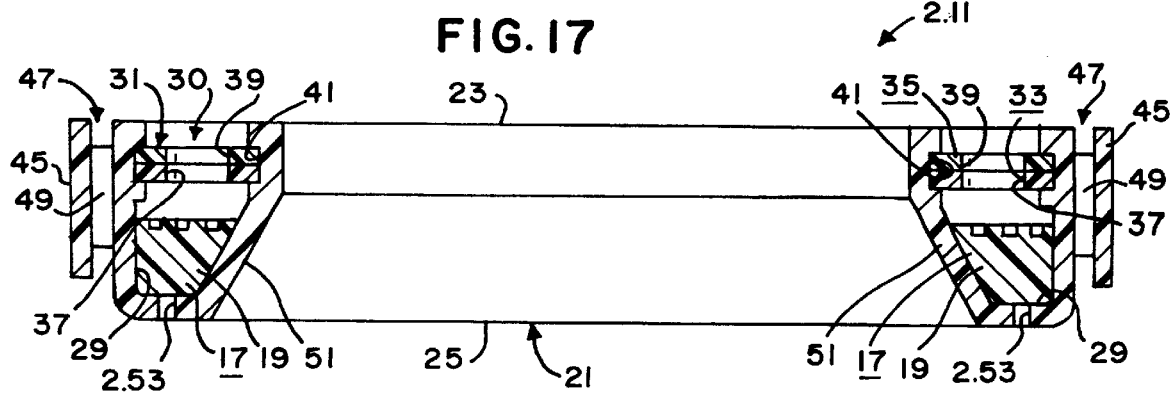

CONTROLLED FRAGRANCE DISPENSER FOR LIGHT BULB

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to a device for setting on a light bulb to dispense fragrance in a controlled manner and in response to heat generated by the light bulb.

2. Information Disclosure Statement

A preliminary patentability search produced the following patents which appear to be relevant to the present invention:

Haensel, U.S. Pat. No. 3,930,796, issued Jan. 6, 1976, discloses an electric lamp bulb having a covering of active oxidation catalyst such that fumes and odors in the confines of a room that are drawn over the catalytic surface will be converted to less objectional products.

Lindauer et al., U.S. Pat. No. 4,184,099, issued Jan. 15, 1980, discloses a ring or toroid formed of a relatively rigid Versalon® type polyamide resin containing volatile substances such as perfume oil, odorants, insecticides, bactericides and animal repellents. The toroid is disclosed as being wrapped around the surface of an electric light bulb, so that when the light bulb is energized, the light bulb will emit perfume into the atmosphere.

Gyulay, U.S. Pat. No. 4,647,428, issued Mar. 3, 1987, discloses a porous ceramic ring sized to be supported on the upper end of an upright light bulb. The ring has a cavity on the top side thereof for holding a predetermined volume of a fragrant oil. The oil will be absorbed by the ring. When the light bulb is energized, the oil absorbed by the ring will be vaporized due to the heat applied thereto by the light bulb.

Spector, U.S. Pat. No. 4,647,433, issued Mar. 3, 1987, discloses a capsule for being attached to the surface of an incandescent light bulb. The capsule includes a flexible pad of porous material impregnated with a volatile liquid fragrances, sandwiched between a base and a cover formed of a metal foil-plastic laminate. The cover has a vent hole therein. The base is coated with a layer of pressure-sensitive adhesive whereby the capsule may be adhered to the surface of the light bulb. Heat from the light bulb will volatilize the liquid impregnant to produce an aromatic vapor that is discharged through the vent hole.

Huff, U.S. Pat. No. 5,908,231, issued Jun. 1, 1999, discloses an absorbent pad made from a non-combustible material such as Manniglas 1200™ for fitting over and securely gripping a light bulb at its widest point. Drops of fragrance oil are placed on the absorbent pad either after or before the absorbent pad is placed on the light bulb. When the light bulb is turned on, the absorbed fragrance oil will be vaporized due to the heat generated by the light bulb.

"Light ring" type fragrance dispensers that emit a fragrance when placed on a light bulb have been available for several years. However, all know prior art "light ring" type fragrance dispensers have certain disadvantages. For example, most prior art "light ring" type fragrance dispensers cause the fragrance medium (typically a fragrant oil) to touch the light bulb, thus reducing the lift of the light bulb. Also, the common prior art "light ring" type fragrance dispensers are made of felt material that have the risk of burning. In addition, with prior art "light ring" type fragrance dispensers, the amount of fragrance has never been controllable; with such prior art "light ring" type fragrance dispensers the fragrance is typically strong at first and then fades out over time.

Nothing in the known prior art discloses or suggests the present invention. More specifically, nothing in the known prior art discloses or suggests a fragrance dispenser including a body member having an opening for receiving a portion of a light bulb and having a cavity for holding a fragrance medium so that when the fragrance medium is held in the cavity, the light bulb is energized, and at least a portion of the light bulb is received in the opening the body member, heat from the light bulb will be transferred through at least a portion of the body member to the fragrance medium held in the cavity in the body member to cause the fragrance medium to emit a fragrance; and including control means for controlling the emissions of fragrance from the fragrance medium held in the cavity in the body member.

BRIEF SUMMARY OF THE INVENTION

The present invention provides a fragrance dispenser for use with a light bulb to dispense fragrance in a controlled manner and in response to heat generated by the light bulb.

The fragrance dispenser of the present invention comprises, in general, a body member having an opening for receiving a portion of a light bulb and having a cavity for holding a fragrance medium so that when the fragrance medium is held in the cavity, the light bulb is energized, and at least a portion of the light bulb is received in the opening the body member, heat from the light bulb will be transferred through at least a portion of the body member to the fragrance medium held in the cavity in the body member to cause the fragrance medium to emit a fragrance; and control means for controlling the emissions of fragrance from the fragrance medium held in the cavity in the body member.

One object of the present invention is to provide a so-called "light ring" type fragrance dispenser for use with a light bulb and that allows the amount of fragrance put out to be controlled.

Another object of the present invention is to provide such a fragrance dispenser in which the fragrance medium (e.g., fragrant oil, etc.) never touches the light bulb so that the life of the light bulb by coming in contact with the fragrance medium.

Another object of the present invention is to provide such a fragrance dispenser in which all portions thereof that come in contact with the light bulb are constructed of highly heat and flame resistant material to thereby reduce the risk of burning.

Another object of the present invention is to provide such a fragrance dispenser in which the fragrance medium (e.g., fragrant oil, etc.) is fully contained or positioned within the dispenser so that the likelihood of spillage of the fragrance medium in the event the fragrance dispenser is dropped or knock-off the light bulb is reduced to a minimum, thereby reducing the possibility of burning or damage to furniture, floors, etc., caused by spillage of fragrance medium.

BRIEF DESCRIPTION OF THE SEVERAL VIEWS OF THE DRAWINGS

FIG. 4 is a top plan view of the fragrance dispenser of FIG. 1, showing the cover fully closed.

FIG. 5 is a sectional view of the fragrance dispenser of FIG. 1 as taken on line 5—5 of FIG. 4, on a somewhat enlarged scale with respect to FIG. 4

FIG. 6 is a top plan view of the fragrance dispenser FIG. 1, similar to FIG. 4 but showing the cover partially opened.

FIG. 7 is a sectional view of the fragrance dispenser of FIG. 1 substantially as taken on line 7—7 of FIG. 6, on a somewhat enlarged scale with respect to FIG. 6.

FIG. 15 is a perspective view of a second preferred embodiment of the fragrance dispenser of the present invention, viewed generally from the bottom.

FIG. 16 is a perspective view of a possible embodiment of a fragrance medium for the fragrance dispenser of FIGS. 1 or 15.

FIG. 17 is a sectional view similar to FIG. 3 with the cover fully opened, but showing the fragrance dispenser of FIG. 15 and the fragrance medium of FIG. 16.

DETAILED DESCRIPTION OF THE INVENTION

Figure 1:
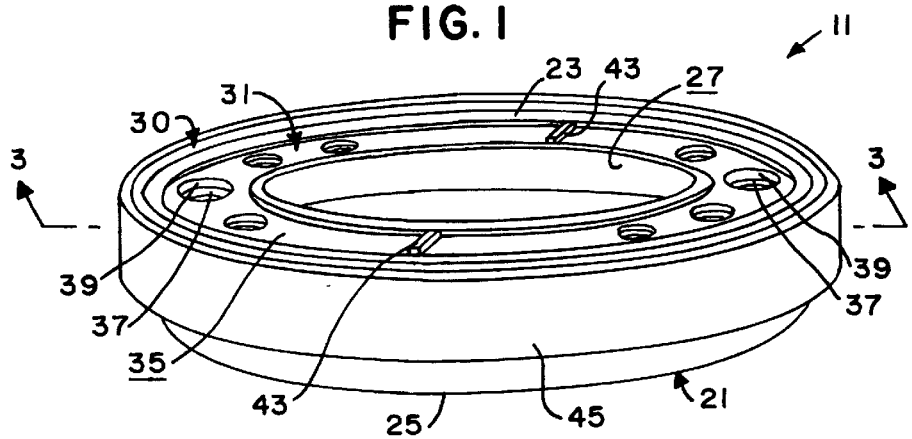
FIG. 1 is a perspective view of a preferred embodiment of the fragrance dispenser of the present invention, viewed generally from the top and showing the cover fully opened.
Figure 2:
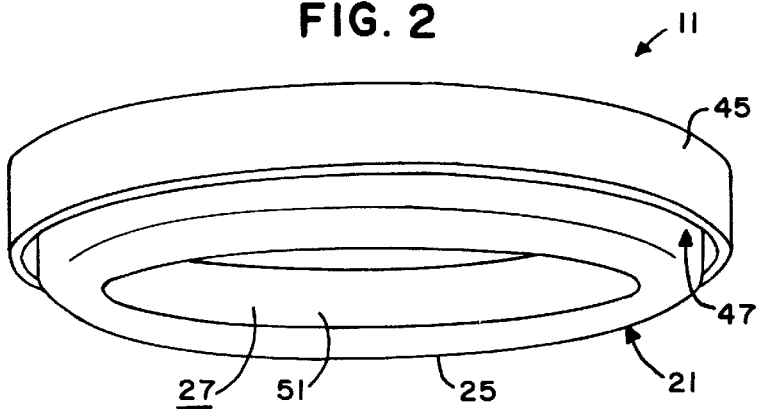
FIG. 2 is a perspective view of the fragrance dispenser of FIG. 1, viewed generally from the bottom.

A first preferred embodiment of the fragrance dispenser of the present invention is shown in FIGS. 1–14, and identified by the numeral 11. The fragrance dispenser 11 is for use with a light bulb 13 having a bulb portion 15, and with a fragrance medium 17 that emits a fragrance when heated.

The light bulb 13 may be any well-know incandescent lamp or the like of standard wattage, etc.

Figure 3:
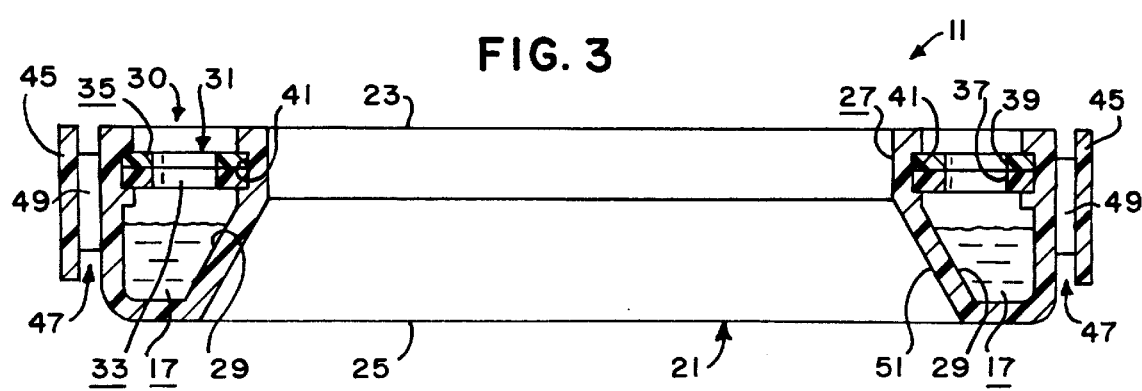
FIG. 3 is a sectional view of the fragrance dispenser of FIG. 1 substantially as taken on line 3—3 of FIG. 1, on a somewhat enlarged scale with respect to FIG. 1, showing the cover fully opened.
Figure 8:
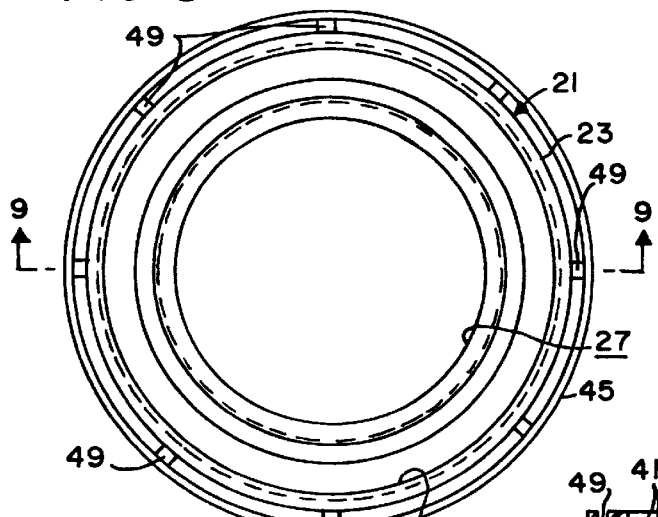
FIG. 8 is a top plan view of the body member of the fragrance dispenser of FIG. 1.
Figure 10:
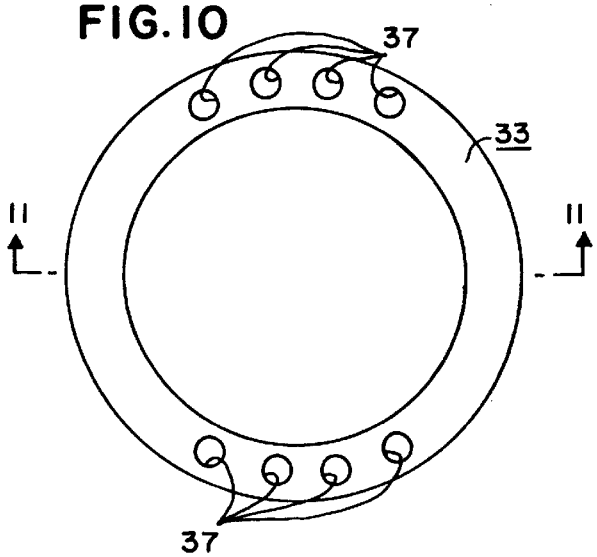
FIG. 10 is a top plan view of a bottom annular plate of the cover of the fragrance dispenser of FIG. 1.

The fragrance medium 17 may consist of a well know fragrant fluid, sometimes called perfume oil or fragrant oil, such as disclosed at column 5, lines 26–47 of Lindauer et al., U.S. Pat. No. 4,184,099, issued Jan. 15, 1980, incorporated herein by reference. The fragrance medium 17 may consist of a liquid or gel per se added or pour into the fragrance dispenser 11 as illustrated in FIGS. 3, 5 and 7, or may include a porous substance such as felt, foam, sponge or other natural or synthetic material that holds a fragrant oil or gel substance. FIGS. 16 and 17 show a possible embodiment of a fragrance medium 17 that includes a ring or annular insert 19 for being inserted into and used in combination with the fragrance dispenser 11. The insert 19 is preferably made out of a solid plastic with a plurality of grooves in the top thereof and with a heat activated fragrance such as perfume or the like embedded therein so that when heat hits it, the perfume is disbursed.

The fragrance dispenser 11 includes a body member 21 having a first side 23, a second side 25, an opening 27 extending between the first and second sides 23, 25, and a cavity 29 in the first side 23 for holding the fragrance medium 17. While the fragrance dispenser 11 can be arranged in various positions with respect to a light bulb 13, etc., the typical position will be with the light bulb 13 facing upward as a typical lamp, with the first side 23 facing upward as the top side of the body member 21, and with the second side 25 facing downward as the bottom side of the body member 21 (see FIG. 14), and for clarity, the first side 23 of the body member 21 will hereinafter be primarily identified as the top side 23, and the second side 25 of the body member 21 will hereinafter be primarily identified as the bottom side 25. The opening 27 extending between the top and bottom sides 23, 25 of the body member 21 is sized to receive at least a portion of the bulb portion 15 of the light bulb 13 as clearly shown in FIG. 14 so that when the fragrance medium 17 is held in the cavity 29 in the top side 23 of the body member 21, the light bulb 13 is energized, and at least a portion of the bulb portion 15 of the light bulb 15 is received in the opening 27 extending between the top and bottom sides 23, 25 of the body member 21, heat from the light bulb 13 will be transferred through at least a portion of the body member 21 to the fragrance medium 17 held in the cavity 29 in the top side 23 of the body member 21 to cause the fragrance medium 17 to emit a fragrance.

The fragrance dispenser 11 includes control means 30 for controlling the emissions of fragrance from the fragrance medium 17 held in the cavity 29 in the top side 23 of the body member 21. The control means 30 could be fixed to allow a predetermined or set amount of fragrance to be emitted from the fragrance medium 17 held in the cavity 29 in the top side 23 of the body member 21. Thus, for example, the control means 30 could consist merely of a plate or the like for covering the cavity 29 in the top side 23 of the body member 21, the plate having one or more holes therethrough of predetermined or set size and spacing, etc., to allow a predetermined or set amount of fragrance to be emitted from the fragrance medium 17 held in the cavity 29 in the top side 23 of the body member 21. However, the control means 30 is preferably adjustable for movement between a fully closed position to prevent any emissions of fragrance from the fragrance medium 17 therethrough, a fully opened position to allow full or maximum emissions of fragrance from the fragrance medium 17 therethrough, and plurality of positions between fully closed and fully opened to allow partial emission of fragrance from the fragrance medium 17 therethrough.

The control means 30 preferably includes a cover 31 for covering the cavity 29 in the top side 23 of the body member 21. The cover 31 may be removable from the body member 21 by a screw-type connection or by a snap-type connection, or could be permanently joined to the body member 21. The cover 31 preferably includes a first plate 33 attached to the body member 21 for covering the cavity 29 in the body member 21, and a second plate 35 attached to the body member 21 for covering the first plate 33. As hereinabove discussed relative to the top and bottom sides 23, 25 of the body member 21, while the fragrance dispenser 11 can be arranged in various positions with respect to a light bulb 13, the typical position will be with the light bulb 13 facing upward as a typical lamp, with the first plate 33 positioned beneath the second plate 35 (see FIG. 14), and for clarity, the first plate 33 of the cover 31 will hereinafter be primarily identified as the bottom plate 33, and the second plate 35 of the cover 31 will be primarily hereinafter identified as the top plate 35. The bottom plate 33 may have at least one and preferably a plurality of spaced apertures 37 therethrough. The top plate 35 may have at least one and preferably has a plurality of spaced apertures 39 therethrough. The bottom and top plates 33, 35 are preferably movable relative to one another to allow the plurality of spaced apertures 37, 39 though one of the plates 33, 35 to be moved into alignment and out of alignment with the plurality of spaced apertures 37, 39 through the other of the plates 33, 35. Thus, the bottom and top plates 33, 35 can be adjusted as illustrated in FIGS. 1 and 3 so that the spaced apertures 37, 39 are fully aligned with one another and the cover 31 is fully opened to allow the maximum emissions of fragrance from the fragrance medium 17 therethrough. Alternatively, the bottom and top plates 33, 35 can be adjusted as illustrated in FIGS. 4 and 5 so that the spaced apertures 37, 39 are fully out of alignment with one another and the cover 31 is fully closed to prevent any emissions of fragrance from the fragrance medium 17 therethrough. Further, the bottom and top plates 33, 35 can be adjusted as illustrated in FIGS. 6 and 7 so that the spaced apertures 37, 39 are partially aligned with one another in a substantially infinite amount, and the cover 31 is partially opened to allow the partial emission of fragrance from the fragrance medium 17 therethrough as will now be apparent to those skilled in the art. While the specific manner in which the bottom and top plates 33, 35 can be moved relative to one another can vary, the body member 21 preferably has a track 41 in or adjacent the mouth of the cavity 29 for slidably receiving the bottom and top plates 33, 35 so the user of the fragrance dispenser 11 can merely slide the top plate 35 to vary the alignment of the spaced apertures 37, 39 as will now be apparent to those skilled in the art. The top plate 35 preferably has one or more handles or tabs 43 for allowing the user of the fragrance dispenser 11 to easily move the top plate 35 relative to the bottom plate 33 and thereby adjust the alignment of the apertures 37, 39.

The fragrance dispenser 11 may include a band 45 adjacent the outer wall of the body member 21 but spaced therefrom by an air gap 47 to provide heat insulation adjacent the outer wall of the body member 21 so that the band 45 will remain cool even while the light bulb 13 is energized. A number of spaced fin-like members or spacers 49 extend between the band 45 and the outer wall of the body member 21 to join the band 45 to the outer wall of the body member 21.

While the actual shape and size of the fragrance dispenser 11 can vary as will now be apparent to those skilled in the art, the body member 21 is preferably annular or ring-shaped, the cavity 29 in the top side 23 of the body member 21 is preferably annular or ring-shaped, the bottom and top plates 33, 35 of the cover 31 are preferably annular or ring-shaped, and the track 41 in the cavity 29 is preferably annular or ring-shaped to slidably and rotatably accept the bottom and top plates 33, 35. The band 45 is also preferably annular or ring-shaped to encircle the body member 21. The opening 27 is preferably located centrally of the body member 21 and preferably has an outer wall portion 51 that slants or angles slightly inwardly between said bottom side 25 of the body member 21 and the top side 23 thereof and being sized to snugly receive at least a portion of the bulb portion 15 of the light bulb 13 in a generally wedge-like grip to allow the fragrance dispenser 11 to sit securely on the bulb portion 15 of the light bulb 13 in a snug fashion without tilting or cocking to one side. The body member 21 and bottom and top plates 33, 35 of the cover 31 may be constructed in various manners out of various materials as will now be apparent to those skilled in the art. Preferably, the body member 21 and bottom and top plates 33, 35 of the cover 31 are molded or otherwise constructed out a very heat resistant plastic material as will now be apparent to those skilled in the art.

The operation and use of the fragrance dispenser 11 of the present invention should now be apparent to those skilled in the art. Normally, the fragrance medium 17, either fluid or gel per se, or some fragrance vehicle for holding fragrance oil or the like such as felt, foam, sponge or the ring 19, etc., is first positioned within the cavity 29 in the body member 21, and the body member 21 is then placed on top of a light bulb 13 so that the fragrance dispenser 11 will sit securely on the bulb portion 15 of the light bulb 13 in a snug fashion. Next, using the tabs 43, the top plate 35 of the cover 31 can be moved relative to the bottom plate 33 thereof so that the apertures 37, 39 move into or out of alignment to control the emissions of fragrance from the fragrance medium 17 held in the cavity 29

Figure 9:
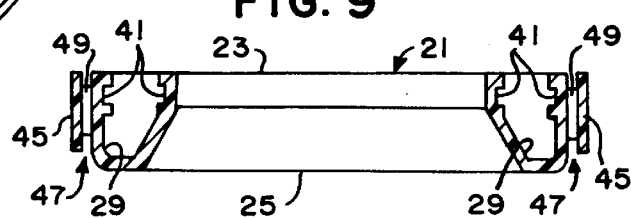
FIG. 9 is a sectional view of the body member of the fragrance dispenser of FIG. 1 substantially as taken on line 9—9 of FIG. 8.
Figure 9A:
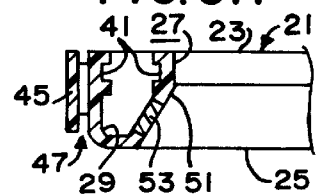
FIG. 9A is a sectional view of a body member of the fragrance dispenser of the present invention similar to FIG. 9, but showing a modified embodiment thereof.
Figure 11:
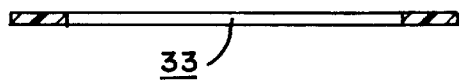
FIG. 11 is a sectional view of the bottom annular plate of the cover of the fragrance dispenser of FIG. 1 substantially as taken on line 11—11 of FIG. 10.
Figure 12:
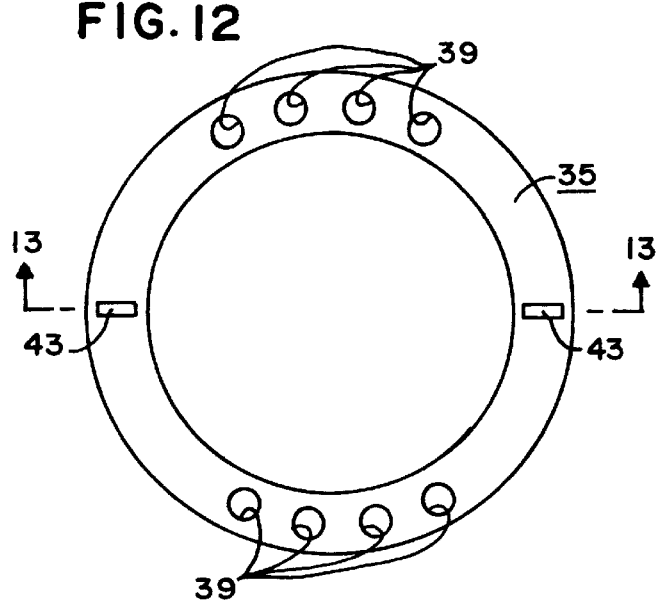
FIG. 12 s a top plan view of a top annular plate of the cover of the fragrance dispenser of FIG. 1.
Figure 13:
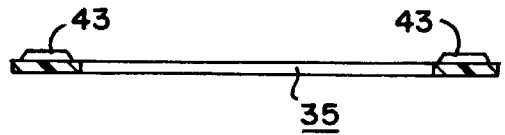
FIG. 13 is a sectional view of the top annular plate of the cover of the fragrance dispenser of FIG. 1 substantially as taken on line 13—13 of FIG. 12.
Figure 14:
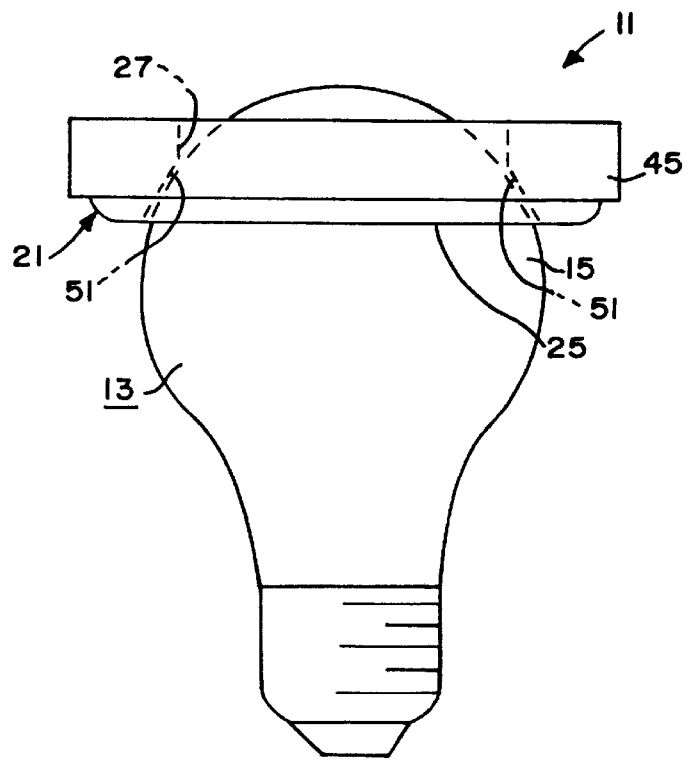
FIG. 14 is a somewhat diagrammatic elevational view of the fragrance dispenser of FIG. 1 shown mounted on a light bulb.

As shown in the modified embodiment of FIG. 9A, the fragrance dispenser 11 may include one or more heat transfer inserts 53 embedded in or mounted on the body member 21 for maximizing or increasing the transfer of heat from the light bulb 13 to the fragrance medium 17 held within the cavity 29 of the body member 21. The heat transfer inserts 53 may be made out of glass, metal, or any material that conducts heat better than the body member 21 and that does not get so hot as to bust the light bulb 11 or melt the plastic out of which the body member 21 is constructed.

A second preferred embodiment of the fragrance dispenser of the present invention is shown in FIGS. 15 and 17, and identified by the numeral 2.11. The fragrance dispenser 2.11 is substantially identical to the fragrance dispenser 11 and the same reference numerals are used with respect to the fragrance dispenser 2.11 as used with the fragrance dispenser 11. The only basic difference between the fragrance dispenser 2.11 and the fragrance dispenser 11 is the plurality of tiny holes 2.53 in the bottom side 25 of the body member 21 extending to the opening 27. Reference should be made to the above description of the fragrance dispenser 11 for a complete and thorough understanding of the construction and function of the fragrance dispenser 2.11.

Although the present invention has been described and illustrated with respect to preferred embodiments and preferred uses therefor, it is not to be so limited since modifications and changes can be made therein which are within the full intended scope of the invention.

What is claimed is:

1. A fragrance dispenser for use with a light bulb having a bulb portion, and with a fragrance medium that emits a fragrance when heated; said fragrance dispenser comprising:

(a) a body member having a first side, a second side, an opening extending between said first and second sides, and a cavity in said first side for holding the fragrance medium so that when the fragrance medium is held in said cavity in said first side of said body member, the light bulb is energized, and said body member is located adjacent the bulb portion of the light bulb, heat from the light bulb will be transferred through at least a portion of said body member to the fragrance medium held in said cavity in said first side of said body member to cause the fragrance medium to emit a fragrance; and (b) adjustable control means for controlling the emissions of fragrance from the fragrance medium held in said cavity in said first side of said body member, said control means being movable between at least two positions to allow the emission of fragrance from the fragrance medium held in said cavity in said first side of said body member to be adjusted between at least two amounts.

2. The fragrance dispenser of claim 1 in which said control means includes a cover for covering said cavity in said first side of said body member.

3. A fragrance dispenser for use with a light bulb having a bulb portion, and with a fragrance medium that emits a fragrance when heated; said fragrance dispenser comprising:

(a) a body member having a first side, a second side, and a cavity in said first side for holding the fragrance medium, (b) a first plate attached to said body member for covering the cavity in said body member, and (c) a second plate attached to said body member for covering said first plate; said first plate having at least one aperture therethrough; said second plate having at least one aperture therethrough; said first and second plates being movable relative to one another to allow said at least one aperture through said second plate to be moved into alignment and out of alignment with said at least one aperture through said first plate to adjustably control the amount of emission of fragrance from the fragrance medium held in said cavity in said first side of said body member.

* * * * *